United States Patent
Weimer et al.

(10) Patent No.: US 6,183,999 B1
(45) Date of Patent: Feb. 6, 2001

(54) PROCEDURE FOR THE DETECTION OF HIGH VIRUS CONCENTRATIONS IN BLOOD PLASMA AND/OR BLOOD SERUM BY MEANS OF THE POLYMERASE CHAIN REACTION

(75) Inventors: Thomas Weimer, Gladenbach; Albrecht Groener, Seeheim, both of (DE)

(73) Assignee: Aventis Behring GmbH, Marburg (DE)

( * ) Notice: Under 35 U.S.C. 154(b), the term of this patent shall be extended for 0 days.

(21) Appl. No.: 09/198,243

(22) Filed: Nov. 24, 1998

(30) Foreign Application Priority Data

Nov. 28, 1997 (DE) .............................. 197 52 898

(51) Int. Cl.$^7$ .............................. C12P 19/34; C12Q 1/68; C07H 21/04
(52) U.S. Cl. .............................. 435/91.2; 435/6; 536/24.3
(58) Field of Search .................................. 435/5, 91.2, 6; 536/24.3, 24.31, 26.6

(56) References Cited

U.S. PATENT DOCUMENTS 5,538,848 * 7/1996 Livak et al. .............................. 435/5

FOREIGN PATENT DOCUMENTS

WO 92/02638  2/1992  (WO) .

OTHER PUBLICATIONS

Clewley, J.P., "Polymerase Chain Reaction Assay of Parvovirus B19 DNA in Clinical Specimens," Journal of Clinical Microbiology, 1989, vol. 27, No. 12, pp. 2647–2651.*
Gartner et al, "PCR Technology for HAV and Parvovirus B19 Plasmapool Testing," Vox Sanguinis, 1998, 1094.*
H.A. Erlich et al., "Recent Advances in the Polymerase Chain Reaction", Science 252: 1643–1651, (1991).
PCR Protocols, "Current Methods and Applications", edited by B.A. White, Humana Press, Totowa, New Jersey, ISBN 0–89603–244–2, vii–ix, (1993).
K.J. Livak et al., "Oligonucleotides with Fluorescent Dyes at Opposite Ends Provide a Quenched Probe System Useful for Detecting PCR Product and Nucleic Acid Hybridization", PCR Methods and Applications, 4:357–362, (1995).
M. Ishizawa et al., "Simple procedure of DNA isolation from human serum", Nucleic Acids Research, 19:5792, (1991).
Gerna, G.; Percivalle, E.; Baldanti, F.; Sarasini, A.; Zavattoni, M.; Furione, M.; Torsellini, M.; and Revello, M.G., "Diagnostic Significance and Clinical Impact of Quantitative Assays for Diagnosis of Human Cytomegalovirus Infection/Disease in Immunocompromised Patients," *Microbiologica,* vol. 21, pp. 293–308 (1998).
Roth, Willi Roth; Weber, Marijke; and Seifried, Erhard, "Feasibility and efficacy of routine PCR screening of blood donations for hepatitis C virus, hepatitis B virus, and HIV–1 in a blood–bank setting," *The Lancet,* vol. 353, pp. 359–363, Jan. 30, 1999.
Chemical Abstracts 121 293833r; (1994) Yamamoto Shuji et al.

* cited by examiner

*Primary Examiner*—John S. Brusca
*Assistant Examiner*—Young Kim
(74) *Attorney, Agent, or Firm*—Finnegan, Henderson, Farabow, Garrett & Dunner, L.L.P.

(57) ABSTRACT

A procedure for the detection of high virus concentrations in blood plasma and/or blood serum by means of the polymerase chain reaction (PCR) is described, in which the sensitivity of the PCR is restricted by the use of suboptimal nucleic acid extraction, amplification or detection conditions. This procedure is suitable, for example, for the detection of parvovirus DNA in plasma or serum, it being possible to adjust the sensitivity of the PCR such that the parvovirus DNA is only detected in samples whose DNA content is greater than $10^6$ to $10^7$ genome equivalents/ml. The detection of the parvovirus DNA amplification carried out is carried out in the sample by measurements of the fluorescence.

6 Claims, No Drawings

SEQUENCE LISTING

<160> NUMBER OF SEQ ID NOS: 3

<210> SEQ ID NO 1
<211> LENGTH: 22
<212> TYPE: DNA
<213> ORGANISM: Parvovirus B19
<220> FEATURE:
<223> OTHER INFORMATION:

<400> SEQUENCE: 1
atgggccgcc aagtacagga aa                    22

<210> SEQ ID NO 2
<211> LENGTH: 23

-continued

```
<212> TYPE: DNA
<213> ORGANISM: Parvovirus B19
<220> FEATURE:
<223> OTHER INFORMATION:

<400> SEQUENCE: 2
caggcacagc tacacttcca ggc                                    23

<210> SEQ ID NO 3
<211> LENGTH: 26
<212> TYPE: DNA
<213> ORGANISM: Parvovirus B19
<220> FEATURE:
<223> OTHER INFORMATION:
<220> FEATURE:
<221> NAME/KEY: modified_base
<222> LOCATION: (1)
<223> OTHER INFORMATION: FAM, carboxy fluorescein substitution
<220> FEATURE:
<221> NAME/KEY: modified_base
<222> LOCATION: (26)
<223> OTHER INFORMATION: TAMRA, carboxytetramethylrhodamine substitution

<400> SEQUENCE: 3
tggtggtctg ggatgaaggt attatt                                 26
```

PROCEDURE FOR THE DETECTION OF HIGH VIRUS CONCENTRATIONS IN BLOOD PLASMA AND/OR BLOOD SERUM BY MEANS OF THE POLYMERASE CHAIN REACTION

The invention relates to a procedure for the detection of high virus concentrations in blood plasma and/or blood serum by means of the polymerase chain reaction, the detection of parvoviruses, in particular of parvovirus B19, being of particular importance.

It is known that viral contaminants which are contained in plasma protein solutions also can pass into the plasma products prepared therefrom and then can lead to infections in patients to whom blood plasma products of this type are administered. In order to prevent this danger, various safety measures have been developed. Among them, the examination of the donor for certain virus infections and the inactivation and elimination of viruses before, during and after the production of the plasma products from the donor blood have been given very particular importance.

Frequently, donor blood is contaminated with parvovirus B19. Parvoviruses lead to serious disorders only in exceptional cases, but for safety reasons donor blood which is contaminated with high titers of parvoviruses should not be used for the production of plasma products. On the other hand, low titers of parvoviruses are tolerable in donor blood, because physical and chemical methods are available with which small residual amounts of viruses in the plasma to be processed can be removed during the preparation of plasma proteins.

It is therefore desirable to identify donor blood having exceptionally high concentrations of parvoviruses in time and to exclude it from processing into plasma products.

It was therefore the object to develop a detection procedure for high-titer plasma protein solutions which only indicates the presence of exceptionally large amounts of pathogenic viruses, in particular of parvoviruses, but in the presence of small amounts of parvoviruses shows no reaction.

As is known, the polymerase chain reaction (PCR) is a very effective method for the detection of small amounts of a known nucleic acid sequence in a sample (Erlich H. A., Gelfand D., Sninsky J. J. (1991), Science 252, pp. 1643–1651; PCR Protocols. Current methods and applications (1993) edited by B. A. White, Humana Press, Totowa, N.J., ISBN 0-89603-244-2). If the sequence of the virus DNA is already known, a primer pair can be synthesized which is complementary to regions on single strands lying opposite to one another and flanks the desired DNA sequence. Under the conditions known per se of a PCR, large amounts of a specific DNA can then be amplified in vitro by succession of, as a rule, more than 30 reaction cycles. By means of the PCR cycles, a DNA fragment of a specific size, which is composed of the lengths of the two primers plus the length of the virus DNA between them, is only amplified if the desired virus DNA is present in the sample.

The PCR technique is so sensitive that using it extremely small amounts of the DNA can be detected with great reliability. The great sensitivity of the PCR also leads to positive results if the virus DNA to be detected is present in a plasma sample in such small amounts that as a result the practical usefulness of the donation, from which the sample derives, for the preparation of blood plasma products is not adversely affected. For example, the customary qualitative PCR technique is not suitable for the detection of the parvovirus B19 DNA, since no differentiation can be made between high and low parvovirus B19 concentrations and also plasma samples having a low parvovirus B19 titer appear to be strongly virally contaminated.

It has now been found that the procedure for the detection of high concentrations of viruses in blood plasma and/or blood serum by means of the polymerase chain reaction can be efficiently modified for practical use if the sensitivity of the polymerase chain reaction is restricted by the use of suboptimal nucleic acid extraction, amplification or detection conditions.

This procedure is suitable for the detection of high concentrations of nucleic acids of pathogenic viruses. The use of this procedure is particularly advantageous for the detection of high nucleic acid concentrations of parvoviruses. According to the invention, the sensitivity of the PCR for the detection of the nucleic acids of parvoviruses is so greatly restricted that the nucleic acids of the parvoviruses can only be detected in samples whose DNA content is greater than $10^6$ to $10^7$ genome equivalents. Samples having a lower parvovirus DNA content are no longer recognized as positive and can be subjected to further processing to give plasma products if small amounts of parvovirus possibly still present are removed during the production procedure.

Several procedures are available for restricting the sensitivity of the PCR. Thus it is possible, for example, to carry out the nucleic acid extraction under conditions in which only small amounts of nucleic acids are isolated or it is possible to work with highly dilute solutions in which only small amounts of nucleic acids are contained. Suboptimal amplification conditions can be established, for example, by carrying out the addition of the primers to the DNA single strand (annealing) and the amplification at unusually low temperatures and restricting the number of the PCR cycles or "slowing down" the amplification by reproduction of the primer concentration below the optimal range. Finally, it is also possible to select the detection conditions such that only particularly high concentrations of parvovirus DNA are recognized.

As is known, the customary PCR begins with a denaturation of the nucleic acids extracted from the investigation sample at 90° C. or higher, for, for example, 20 seconds to 1 minute.

In the course of this, these are split up into single strands, to which the primers are normally added at a temperature of 45 to 650° C. The amplification is then carried out at 72° C.

In contrast, according to the invention the annealing and/or the amplification is carried out at a temperature of about 52° C. Additionally, the number of PCR cycles is restricted to 30. By this means, the reaction rate of the PCR is considerably restricted and the amount of the parvovirus DNA formed is considerably reduced by the reduction of the number of cycles.

The primers employed are, for example, the following oligonucleotides.

SEQ ID NO. 1: $5'$ATG GGC CGC CAA GTA CAG G A$^{3'}$

SEQ ID No. 2: $5'$CAG GCA CAG CTA CAC TTC CAG GC$^{3'}$

It has now proven to be particularly advantageous in the procedure according to the invention to carry out the detection of the amplified parvovirus DNA section by means of a probe which carries two fluorescent dyes. This labeled probe, which is added to the DNA between the two primers characterized by the abovementioned sequences, then has, for example, the following sequence:

SEQ ID No. 3: $5'$FAM-TGG TGG TCT GGG ATG AAG GTA TTA TT-TAMRA$^{3'}$

This sequence can be obtained commercially under the name TaqMan® and is intended for use in the 5'-nuclease assay, the TaqMan Assay. This method is described in detail by Livak K. J., Flood S. J. A., Marmaro J., Giusti W., Deetz K., Oligonucleotides with fluorescent dyes at opposite ends provide a quenched probe system useful for detecting PCR product and nucleic acid hybridization. PCR Method and Appl. 1995; 4:357–362 and which is incorporated by reference.

The particular characteristic of this probe is that the fluorescence of the (FAM) attached to the 5' end of the probe, the reporter, is reduced by the vicinity of the second fluorescent dye (TAMRA), the quencher, arranged at the 3' end of the primer.

In the course of the amplification, the new DNA strand is formed under the action of a thermostable DNA polymerase, preferably of Taq DNA polymerase. In the course of this, the DNA polymerase displaces the probe not only from the single strand, but splits it up by means of its endonucleolytic activity and at the same time liberates the two fluorescent dyes. The fluorescence of the reporter dye is now no longer suppressed by the quencher dye and increases. If the fluorescence at the reporter wavelength and at the quencher wavelength (518 nm for FAM and 582 nm for TAMRA) is now measured using a fluorescence spectrometer, the quotient of reporter and quencher value can be formed (RQ). The mean value of the quotients of several negative controls (RQ⁻) is subtracted therefrom and the calculated value is designated as ΔRQ. The method for the recognition of DNA formation in the PCR by the use of a primer labeled with two fluorescent dyes is described in the International Patent Application WO 92/02638 which is incorporated by reference.

If this process for the detection of the parvovirus B19 DNA is employed in the PCR procedure with restricted sensitivity according to the invention, samples having a ΔRQ value of greater than or equal to 0.7 are assessed as positive and separated. Samples having a low ΔRQ value contain small amounts of parvovirus B19 DNA (<$10^6$ to $10^7$ genome equivalents/ml).

The invention is illustrated by the following example:

EXAMPLE

A Nucleic acid extraction

The nucleic acid extraction is carried out using an improved version of the method described by Ishizawa et al. (Ishizawa M., Kobayashi Y., Miyamura T., Matsuma S.: Simple procedure of DNA isolation from human serum. Nucl. Acids Res. 1991; 19:5792). To this end, 100 μl of plasma or serum are mixed with 300 μl of extraction buffer (6 M sodium iodide, 13 mM EDTA, 0.5% Sarcosyl, 26 mM tris HCl, pH 8.0, 33 μg/ml of glycogen, 77 μg/ml of yeast tRNA) and incubated at 60±2° C. for 15 minutes. The nucleic acids are precipitated at room temperature for 20 minutes by addition of 400 μl of isopropanol. Centrifugation at 13,000 to 14,000 rpm for 10 minutes in a bench top centrifuge for pelleting the nucleic acids follows. The supernatant is discarded, and the pellet (precipitate) is washed with 1 ml of 40% isopropanol, dried and resuspended in 20 μl of $H_2O$.

B Amplification

The amplification of the B19 DNA in the NS1 gene is adjusted by suboptimal annealing and elongation temperatures such that only those samples are positive whose DNA content is greater than $10^6$ to $10^7$ genome equivalents/ml. 40 μl of Master Mix (5 μl of 10×PCR buffer (Perkin-Elmer Catalog 1995/96 PCR Systems, Reagents and Consumables), 3 μl of 25 mM $MgCl_2$, 4 μl of 2.5 mM deoxynucleoside triphosphate, 4 μl each of the oligonucleotides of SEQ ID NO. 1 and SEQ ID NO. 2 (10 pmol/μl each), 0.3 μ of the oligonucleotide of SEQ ID NO. 3 (10 pmol/μl), 0.25 μl of Taq DNA polymerase (1.25 units; Perkin-Elmer Catalog 1995/96 PCR-Systems, Reagents and Consumables), 11.45 μl of $H_2O$) are pipetted into 10 μl of the extracted DNA, mixed and subjected to the following thermal cycles:

1. Initial denaturation for 1 minute at 90° C.
2. 30 cycles, denaturation at 94° C. for 28 seconds and annealing and elongation at 52° C. for 1 minute each
3. Cooling at 4° C. until assessment.

C Evaluation

The PCR reaction is evaluated in a fluorescence spectrometer. To this end, the fluorescence at the reporter wavelength and quencher wavelength (518 nm for FAM or 582 nm for TAMRA) is measured and the respective quotient of reporter value and quencher value is formed (RQ). The mean value of the quotients of three negative controls (RQ-) is subtracted therefrom, and the calculated value is designated as ΔRQ. Samples having a ΔRQ of greater than or equal to 0.7 are assessed as positive, samples of less than 0.7 as negative. By means of this, only those samples are assessed as positive whose DNA content is greater than $10^6$ to $10^7$ genome equivalents/ml.

What is claimed is:

1. A procedure for the detection of high virus concentrations in at least one of blood plasma or blood serum by means of a polymerase chain reaction (PCR), comprising restricting the sensitivity of the PCR, so that only samples of high virus concentrations wherein the viral DNA content of said samples is greater than $10^6$ to $10^7$ genome equivalents/ml are detected and wherein said virus is a parvovirus.

2. The procedure as claimed in claim 1, wherein the parvovirus DNA content is detected by means of fluorescence measurements wherein the ΔRQ value is greater than or equal to 0.7.

3. The procedure as claimed in claim 1, wherein the restriction of sensitivity of the polymerase chain reaction is accomplished during the PCR reaction by use of suboptimal conditions wherein the addition of primers to a DNA single strand (annealing) and amplification take place at a temperature of approximately 52° C. and not more than 30 PCR cycles are carried out.

4. The procedure as claimed in claim 1, wherein the parvovirus DNA used in the PCR is detected by an additional probe which carries two fluorescent dyes, and wherein the fluorescence of one dye (reporter) is reduced by the second dye (quencher) when said additional probe is still intact, and wherein the fluorescence of the reporter increases as soon as said additional probe is displaced by a thermostable DNA polymerase and the fluorescent dyes are released by means of the endonucleolytic activity of said polymerase.

5. The procedure as claimed in claim 4, wherein said thermostable DNA polymerase is a Taq DNA polymerase.

6. The procedure as claimed in claim 3, wherein restricting the sensitivity of the PCR is accomplished by the use of at least one of the suboptimal detection conditions recited therein.

* * * * *